Figure 1:
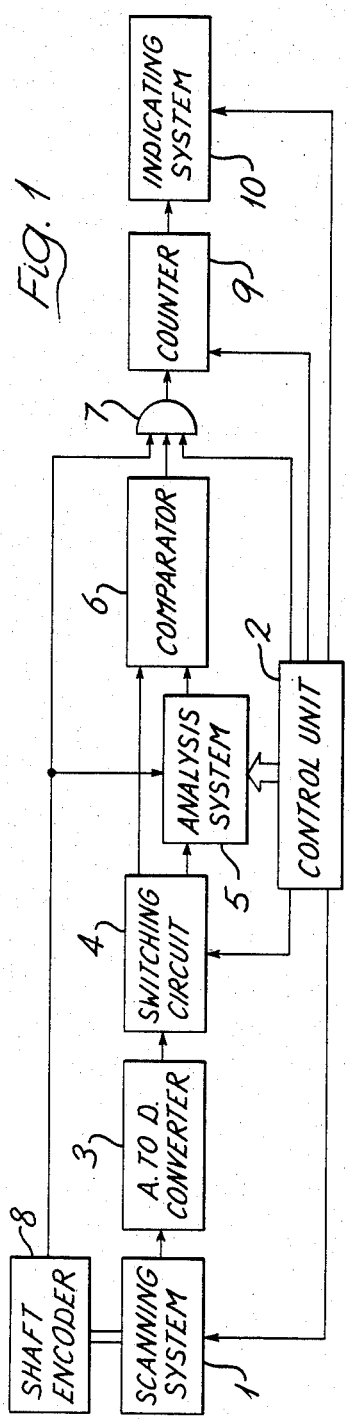

United States Patent [19]

Bailey

[11] Patent Number: 4,512,663
[45] Date of Patent: Apr. 23, 1985

[54] OPTICAL INSPECTION OF MACHINED SURFACES

[75] Inventor: Warren P. N. Bailey, High Wycombe, England

[73] Assignee: National Research Development Corporation, London, England

[21] Appl. No.: 459,032

[22] Filed: Jan. 18, 1983

[30] Foreign Application Priority Data

Jan. 29, 1982 [GB] United Kingdom ............... 8202552

[51] Int. Cl.$^3$ ............................................ G01N 21/88
[52] U.S. Cl. ................................ 356/446; 250/563; 356/237; 356/241
[58] Field of Search ............... 356/237, 241, 429, 430, 356/431, 445, 446, 448; 250/362, 363; 364/470, 507

[56] References Cited

U.S. PATENT DOCUMENTS

| | | |
|---|---|---|
| 3,202,042 | 8/1962 | Jamieson et al. .................. 356/448 |
| 4,055,382 | 10/1977 | Ziekman et al. .................... 356/446 |
| 4,253,768 | 3/1981 | Yaroshuk et al. ............... 250/563 X |
| 4,413,279 | 11/1983 | Gorl ................................. 356/237 X |
| 4,428,672 | 1/1984 | Allard et al. ....................... 356/237 |
| 4,448,527 | 5/1984 | Milana .............................. 356/237 |
| 4,454,542 | 6/1984 | Miyazawa ..................... 356/445 X |

OTHER PUBLICATIONS

Professor P. A. McKeown et al., The Application of Optics to the Quality Control of Automotive Components, Cranfield Institute of Technology, U.K., SPIE (Society of Photo-Optical Instrumentation Engineers), vol. 60, 1975, pp. 77 to 84.

W. Bailey, Optical Inspection of Cylinder Bores, Cranfield Institute of Technology, Tribology International, Dec. 1977, vol. 10, No. 6, pp. 319 to 321.

Primary Examiner—Vincent P. McGraw
Assistant Examiner—S. A. Turner
Attorney, Agent, or Firm—Cushman, Darby & Cushman

[57] ABSTRACT

Defects in a machined surface are detected by sensing excursions in a test signal generated by means of a conventional scanning system (1), which includes a detector responsive to light reflected and/or scattered from an illuminated spot scanned over the surface. The test signal is applied to a comparator (6), together with a signal representative of an appropriate threshold level for sensing the excursions. This level is ascertained, in accordance with a specific formula, by means of an analysis system (5) to which is applied a preliminary signal derived in a similar manner to the test signal from the surface to be inspected.

5 Claims, 3 Drawing Figures

OPTICAL INSPECTION OF MACHINED SURFACES

This invention relates to the optical inspection of machined surfaces, and is concerned in particular with methods of the kind in which a surface undergoing inspection is irradiated with a beam of light to form an illuminated spot which is caused to scan over the surface, an electrical test signal representative of the resultant variations of the proportion of the incident light returned from the illuminated spot is derived by means of a photo-electric detection system, and the presence of defects in the surface is detected by sensing excursions in the test signal corresponding to decreases of said proportion below a preset threshold level. It is to be understood that in this specification the term light includes ultra-violet and infra-red radiation as well as visible radiation.

Methods of the kind specified have been proposed as substitutes for visual inspection, and are of particular interest in the context of quality control of the output of automated manufacturing processes (see for example the paper by McKeown et al. in Proceedings SPIE, Vol. 60, page 77 and the paper by Bailey in Tribology International, December 1977, page 319). With such methods, the data obtainable by sensing the relevant excursions in the test signal may be processed in various ways to provide information relating to the quality of the inspected surface; for example one can simply count the number of relevant excursions in the test signal (or in a portion of it corresponding to a given area of the inspected surface), or one can weight the count in accordance with the duration and/or peak magnitude of the individual excursions.

In a method of the kind specified the threshold level must of course be set at a value sufficiently low to ensure discrimination between excursions of the test signal due to defects of interest and the fluctuations in the test signal which inevitably occur (whether or not defects are present) as a result of the general properties of the surface undergoing inspection; these fluctuations will usually be much more numerous than the excursions which it is desired to sense. Thus, from the point of view of sensitivity of detection of defects, the optimum value for the threshold level is equal to the highest value of the proportion of the incident light returned from the illuminated spot for which there would be a negligible occurrence of sensed excursions in the test signal in the absence of any defects in the inspected surface; this value is subsequently denoted by $L_o$. A difficulty arises, however, in that $L_o$ may vary significantly between similar surfaces of different components of the same type, but cannot be measured directly for a given surface without prior knowledge of whether or not there are defects in that surface; there is thus no direct way in which one can ensure in advance for inspection of a particular surface that the threshold level is set at $L_o$.

The present invention seeks to circumvent this difficulty, and is based on the discovery that it is possible to ascertain $L_o$ at least approximately in respect of a given machined surface by means of an analysis of an electrical signal derived from that surface in a similar manner to that in which the test signal is derived in a method of the kind specified. More specifically, by inspecting such signals to ascertain in each case the fraction N of the total length of the scan for which the value of the proportion of the incident light returned from the illuminated spot falls below a given level L, as may readily be effected by sampling each signal at an appropriate rate and counting the number of samples for which the value of the signal corresponds to a sufficiently low value of said proportion, it has been found from tests on a variety of machined surfaces that the relationship between N and L for a particular surface can be expressed to a good approximation by the equation $$L = L_o + K \ln(N) \tag{1}$$

(where ln (N) denotes the natural logarithm of N and K is a constant whose value varies from surface to surface) over a range of values of L for which the value of N is predominantly determined by the general properties of the surface (i.e. such that N is primarily dependent on the existence of the fluctuations referred to above); this range of values of L of course lies close to, but somewhat above, $L_o$. It follows from the relationship expressed by Equation (1) that, if one analyses the signal derived from a given machined surface to ascertain two corresponding pairs ($L_A, N_A$ and $L_B, N_B$) of values of L and N such that $L_A$ and $L_B$ lie within the range referred to, $L_o$ can be deduced by simple algebra to be given by the equation $$L_o = \frac{L_B \ln(N_A) - L_A \ln(N_B)}{\ln(N_A/N_B)} \tag{2}$$

The analysis can be effected either by using predetermined values of L and finding the corresponding values of N or vice versa.

According to one aspect of the invention, therefore, in the inspection of a machined surface by a method of the kind specified said threshold level is automatically set substantially to the value of $L_o$ given by Equation (2) above in respect of the analysis of an electrical signal derived from said surface in a similar manner to that in which said test signal is derived.

Although it is not essential, it will normally be desirable for the signal which is analysed to ascertain $L_o$ to be derived using the same beam of light and photoelectric detection system as are used for the derivation of the test signal. Where this arrangement is adopted, it would in principle be possible to use a single scan of the inspected surface to generate a basic signal and utilize two versions of this respectively as the signal which is analysed and the test signal; this would, however, require the provision of a facility for storing the version utilised as the test signal for a time sufficient to enable the required analysis to be carried out on the other version and it will therefore usually be preferable to use two consecutive scans of the inspected surface respectively to generate the signal which is analysed and the test signal. In many cases this can conveniently be effected by arranging for the two scans to correspond respectively to movements of the illuminated spot in opposite senses along the same path. Although it will normally be appropriate for the extent of the scan to be the same in respect of both signals, it is envisaged that it would be possible in some cases to obtain sufficient information for the determination of $L_o$ using scanning of only part of the total surface area that is scanned in the inspection method itself.

According to another aspect of the invention there is provided an apparatus for use in the inspection of a machined surface by a method of the kind specified, the apparatus comprising means for analysing an electrical signal derived from said surface in a similar manner to that in which said test signal is derived to obtain data from which $L_o$ may be deduced in accordance with Equation (2) above, and means for utilising said data to develop a further electrical signal representative of the value of $L_o$.

According to a further aspect of the invention there is provided an apparatus for use in the inspection of a machined surface, the apparatus comprising a scanning system incorporating means for causing an illuminated spot formed by a beam of light to scan over a surface to be inspected and a photoelectric detection system responsive to the resultant variations of the proportion of the incident light returned from said spot, means for deriving first and second electrical signals by means of said detection system respectively as a result of consecutive operations of said scanning system in respect of the same surface, means for analysing said first signal to obtain data from which $L_o$ may be deduced in in accordance with Equation (2) above, and means for sensing excursions in said second signal corresponding to decreases of said proportion below a threshold level which is automatically set substantially to the value of $L_o$ indicated by said data.

Figure 2:
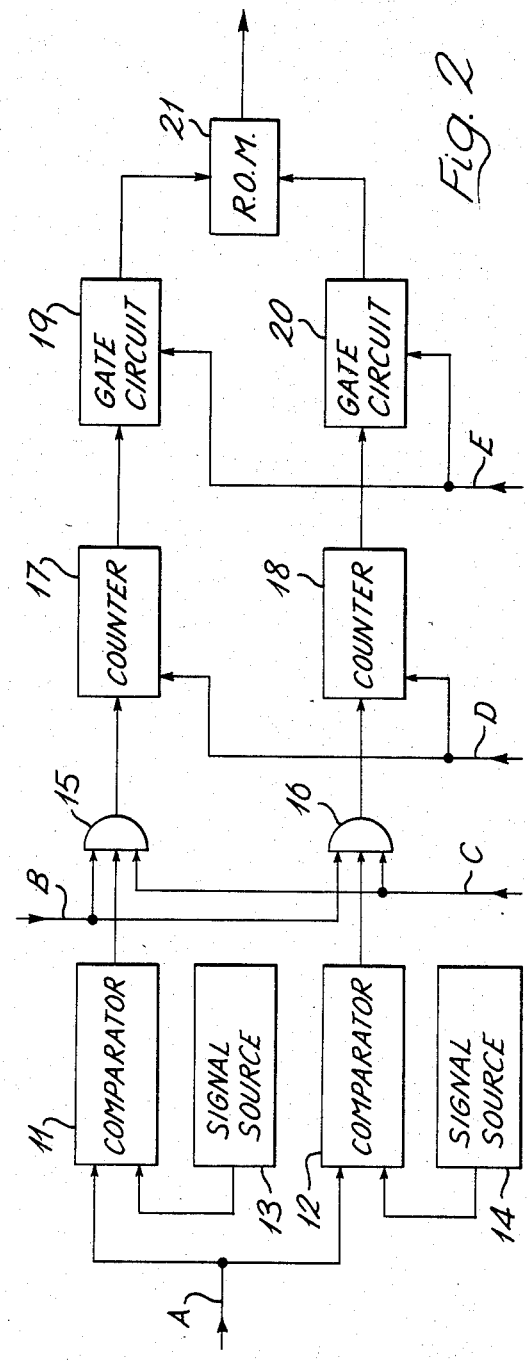
Figure 3:
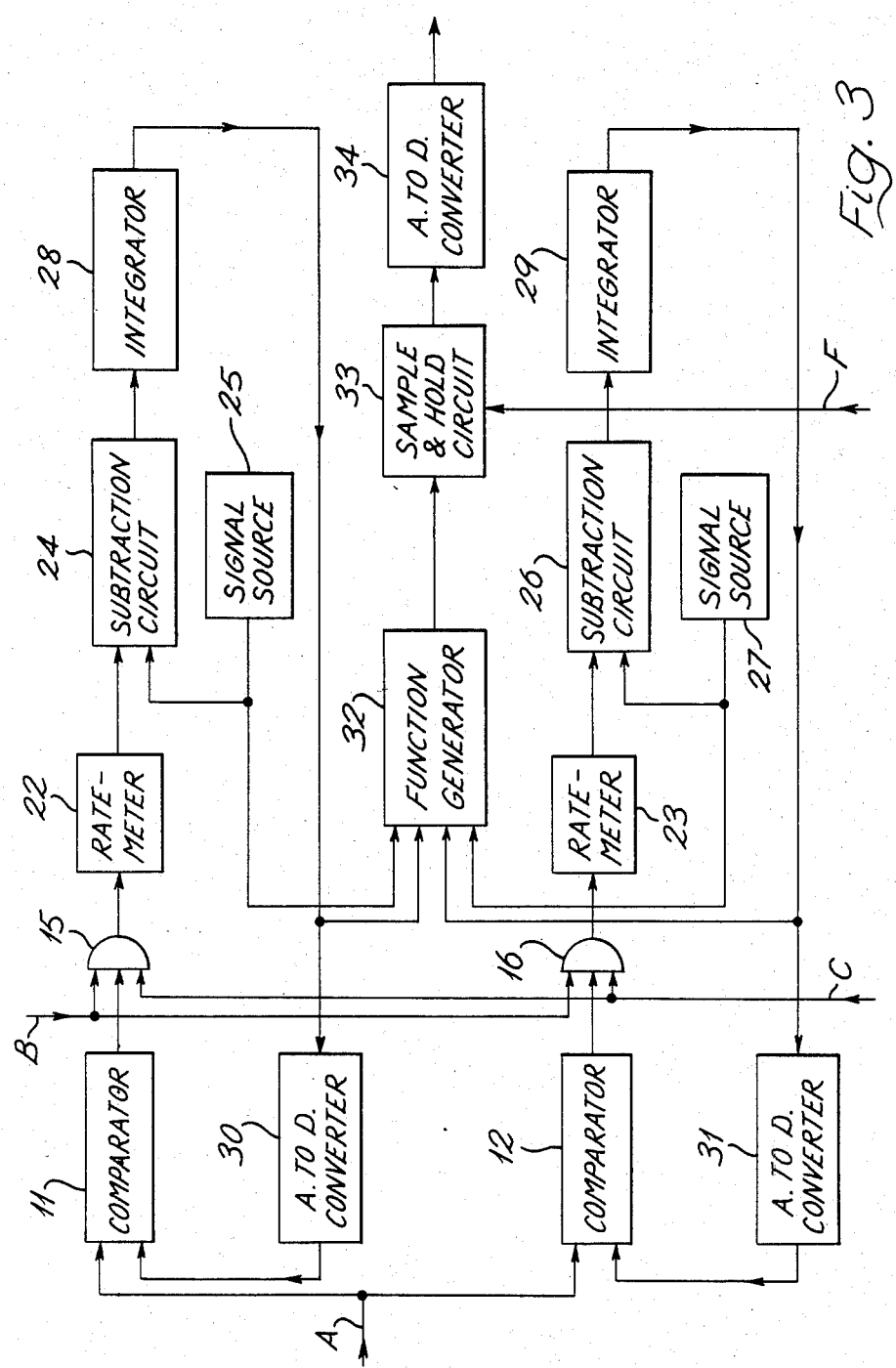

Certain embodiments of the invention will now be described by way of example with reference to the accompanying drawings, in which:

FIG. 1 is a schematic diagram of an apparatus for use in the inspection of machined cylinder bores; and FIGS. 2 and 3 are block diagrams of alternative forms of analysis system suitable for use in the apparatus illustrated in FIG. 1.

Referring to FIG. 1, the apparatus includes a scanning system 1 of conventional form, which may suitably be as described and illustrated in U.S. Pat. No. 4,055,382 (but omitting the secondary detection system incorporating the components 13 and 18–21). Briefly, the system 1 includes a laser source, a beam splitter, a telescopic system incorporating two lenses having a planar deflecting mirror disposed optically between them, a third lens and a photoelectric detector. In use, the source projects a beam of light through the beam splitter initially along the axis of a cylinder bore to be inspected, and the light is focussed and deflected by the telescopic system to form an illuminated spot on the bore surface; light reflected and/or scattered from this spot is returned via the telescopic system to the beam splitter, where it is deflected so as to pass through the third lens and thus be focussed on the detector. The illuminated spot is caused to scan over the bore surface at a constant speed along a helical path having a pitch less than the diameter of the spot, by effecting appropriate synchronized rotational and translational movements of parts of the optical system. The photoelectric detector consequently develops an analogue electrical signal whose value varies, in direct proportion, in accordance with the resultant variations of the proportion of the incident light returned from the illuminated spot.

In using the apparatus illustrated in FIG. 1 to inspect a specific cylinder bore, the scanning system 1 is operated, under the control of signals generated by a control unit 2, so as to perform two consecutive scans of the bore surface with the illuminated spot moving along the same path but respectively in opposite senses for the two scans. The system 1 thus generates in succession first and second signals, respectively during the first and second of the two scans. These signals generated by the signal 1 are fed to an analogue-to-digital converter 3 whose output is applied to a switching circuit 4. The circuit 4 is operated, under the control of signals generated by the unit 2, so that the digital version of the first signal is fed to an analysis system 5 while the digital version of the second signal is fed to a first input of a comparator 6. Suitable forms of construction for the analysis system 5 are described in detail below; at this point it is sufficient to note that the system 5 is operative, under the control of signals generated by the unit 2, to effect an analysis of the first signal and as a result to develop a digital signal which is applied to a second input of the comparator 6 during the second scan, this digital signal having constant value substantially equal to that value of the digital version of the second signal which corresponds to the value of $L_o$ given by Equation (2) above.

The comparator 6 is operative to generate an output signal if, and only if, the value of the signal applied to its first input falls below the value of the signal applied to its second input. The output from the comparator 6 is applied to a first input of an AND gate 7, to a second input of which is applied a train of regularly recurrent pulses generated by a shaft encoder 8 associated with the scanning system 1; the encoder 8 may suitably be arranged so that about one thousand pulses occur during each revolution of the rotational component of the scanning movement. As will be explained more fully below, the output of the encoder 8 is also utilised in the analysis system 5. The gate 7 also has a third input to which there is applied a signal generated by the unit 2, this signal being coterminous with the second scan. Accordingly, during the second scan, whenever the proportion of the incident light returned from the illuminated spot falls for a significant period below the threshold level set by the operation of the analysis system 5, the corresponding excursion in the second signal will result in the appearance at the output of the gate 7 of one or more pulses, each such pulse being synchronous with one of the pulses generated by the encoder 8 and the number of pulses for each relevant excursion being dependent on the duration of that excursion. The pulses appearing at the output of the gate 7 are fed to a counter 9, which is set to zero at the start of the second scan by means of a signal generated by the unit 2; the total count accumulated by the counter 9 during the second scan of course gives an inverse measure of the quality of the inspected cylinder bore in respect of surface defects. A digital signal representative of the value of the count accumulated by the counter 9 is fed to an indicating system 10, which is rendered operative at the end of the second scan, by means of a signal generated by the unit 2, to provide an indication of whether or not the total count is below a predetermined value, and hence whether or not the inspected cylinder bore is of acceptable quality.

Turning now to FIG. 2, there is illustrated therein one form which may be adopted for the analysis system 5 of the apparatus shown in FIG. 1. In this case the system includes a pair of comparators 11 and 12 similar to the comparator 6, to the first inputs of which is applied, over a path A, the digital version of the first signal derived from the scanning system 1. To the second inputs of the comparators 11 and 12 are respectively applied digital signals generated by sources 13 and 14, which respectively have constant values equal to those values of the digital version of the first signal which correspond to different values $L_A$ and $L_B$ of the proportion of the incident light returned from the illuminated spot. The values $L_A$ and $L_B$ are chosen, in the light of the results of preliminary experiments on surfaces of the same type as those to be inspected, so that they lie within the range of values of L for which Equation (1) above will validly represent the relationship between N and L. The outputs from the comparators 11 and 12 are respectively applied to first inputs of a pair of AND gates 15 and 16, to second inputs of which are applied, over a path B, the pulses generated by the shaft encoder 8. Each of the gates 15 and 16 also has a third input to which there is applied, over a path C, a signal generated by the unit 2, this signal being coterminous with the first scan.

The output of the gate 15 thus consists of pulses synchronous with those of the pulses generated by the encoder 8 which occur during the first scan at times when the proportion of the incident light returned from the illuminated spot has a value below the level $L_A$; the output of the gate 16 is of course similar, but with $L_B$ substituted for $L_A$. The outputs of the gates 15 and 16 are respectively applied to a pair of counters 17 and 18 which are set to zero at the start of the first scan by means of a signal generated by the unit 2 and applied over a path D. It will be appreciated that the total counts $C_A$ and $C_B$ respectively accumulated by the counters 17 and 18 during the first scan are respectively approximately equal to $PN_A$ and $PN_B$, where P is the total number of pulses generated by the encoder 8 during the first scan and $N_A$ and $N_B$ are those fractions of the total length of the first scan for which the value of the proportion of the incident light returned from the illuminated spot falls below $L_A$ and $L_B$ respectively.

Digital signals respectively representative of the values of the counts accumulated by the counters 17 and 18 are applied respectively to the inputs of a pair of gate circuits 19 and 20, the outputs of which are utilised to address a read-only memory 21. The gate circuits 19 and 20 are opened for a period extending from the end of the first scan to the end of the second scan, by means of a signal generated by the unit 2 and applied over a path E. The memory 21 has a series of addresses which respectively correspond to different pairs of possible values of $C_A$ and $C_B$; the ranges of these possible values are of course determined (having regard to the values of $L_A$, $L_B$ and P) by the possible range of values of the constant K in Equation (1) for surfaces of the type to be inspected. At each address is stored a digital word representing the value of $L_o$ given by Equation (2) in respect of the corresponding pair of values of $C_A$ and $C_B$ (again having regard to the values of $L_A$, $L_B$ and P). Accordingly, during the period when the gate circuits 19 and 20 are opened, and in particular during the whole of the second scan, the memory 21 will provide a digital output signal representative of the value of $L_o$ given by Equation (2) in respect of the analysis of the first signal generated by the scanning system 1; this digital signal is of course that which is applied to the second input of the comparator 6.

If it is desired to use the apparatus shown in FIG. 1 for the inspection of surfaces of different types while utilising an analysis system of the form illustrated in FIG. 2, it will normally be necessary to have a different memory 21 for each type of surface to be inspected, and it may be necessary to make provision for the sources 13 and 14 to be variable so that $L_A$ and $L_B$ can be selected according to the type of surface being inspected. FIG. 3 illustrates an alternative form which may be adopted for the analysis system where a more flexible arrangement is required.

The system shown in FIG. 3 includes a pair of comparators 11 and 12 and a pair of AND gates 15 and 16 arranged to operate similarly to the corresponding components of the system shown in FIG. 2, with the exception that, instead of the second inputs of the comparators 11 and 12 having applied to them digital signals of constant value, they have applied to them digital signals which (as will be more fully explained below) are arranged to be automatically driven during the first scan respectively to different values which correspond to values of the proportion of the incident light returned from the illuminated spot which lie within the range of values of L for which Equation (1) will validly represent the relationship between N and L. In this case the outputs of the gates 15 and 16 are respectively applied to a pair of ratemeters 22 and 23, each of which develops an output analogue signal whose value is directly proportional to the mean repetition rate of the pulses applied to its input. With this arrangement it will be seen that if the digital signal applied to the second input of one of the comparators 11 and 12 during the first scan is maintained at a value corresponding to a given value of L, then the value of the output signal developed by the corresponding ratemeter 22 or 23 will, to a good approximation, be directly proportional to the corresponding value of N.

The output signal from the ratemeter 22 is fed to a subtraction circuit 24 where it is subtracted from an analogue signal of constant value generated by a variable source 25, the source 25 being set so that this value is equal to the value which the output signal from the ratemeter 22 would have for a specific value of N equal to $N_A$. The output signal from the ratemeter 23 is dealt with similarly, using a subtraction circuit 26 and a variable source 27, but with the source 27 set so that the value of the signal which it generates is equal to the value which the output signal from the ratemeter 23 would have for a different specific value of N equal to $N_B$. For a given type of surface to be inspected, $N_A$ and $N_B$ are chosen so that the corresponding values of L (respectively $L_A$ and $L_B$) lie within the range for which Equation (1) will validly represent the relationship between N and L. The outputs of the subtraction circuits 24 and 26 are fed respectively to a pair of integrators 28 and 29, whose outputs are in turn respectively fed to a pair of analogue-to-digital converters 30 and 31; the outputs of the converters 30 and 31 constitute the digital signals respectively applied to the second inputs of the comparators 11 and 12.

There are thus constituted two servo loops which operate during the first scan so as rapidly to drive the error signals developed by the circuits 24 and 26 to zero and to maintain them substantially at this value for the rest of the first scan. In this condition, the digital signals respectively applied to the second inputs of the comparators 11 and 12 are maintained substantially at values corresponding to the respective levels $L_A$ and $L_B$ given by Equation (1) when N takes the chosen values of $N_A$ and $N_B$; the analogue signals which constitute the respective outputs of the integrators 28 and 29 will of course also have values respectively proportional to $L_A$ and $L_B$ in this condition. These analogue signals, together with the signals generated by the sources 25 and 27, are applied to a function generator 32, which develops an output signal proportional to $$\frac{V_B \ln(N_A) - V_A \ln(N_B)}{\ln(N_A/N_B)},$$

where $N_A$ and $N_B$ are as determined by the settings of the sources 25 and 27 and $V_A$ and $V_B$ are the values of the signals respectively derived from the integrators 28 and 29; the constant of proportionality is chosen so that at the end of the first scan the value of the output signal from the generator 32 will be substantially equal to that value of the signals generated by the system 1 which corresponds to the value of $L_o$ as given by Equation (2). The output of the generator 32 is applied to a sample-and-hold circuit 33 which is operated at the end of the first scan by means of a signal generated by the unit 2 and applied over a path F. The output of the circuit 33 is fed to an analogue-to-digital converter 34, whose output will throughout the second scan be a digital signal representative of the value of $L_o$ given by Equation (2) in respect of the analysis of the first signal generated by the scanning system 1; this digital signal is of course that which is applied to the second input of the comparator 6.

I claim:

1. In a method of inspection of a machined surface, which method comprises deriving an electrical test signal in respect of said surface by causing an illuminated spot formed by a beam of light to scan over said surface and detecting the resultant variations of the proportion of the incident light returned from said spot, and sensing excursions in said test signal corresponding to decreases of said proportion below a preset threshold level:

the improvement comprising setting said threshold level in accordance with the result of an analysis of an electrical signal derived in respect to said surface in a similar manner to that in which said test signal is derived, said threshold level being set substantially to the value given by the expression $$\frac{L_B \ln(N_A) - L_A \ln(N_B)}{\ln(N_A/N_B)},$$

$N_A$ and $N_B$ being different values of N, there N is the fraction of the total length of the scan for which the value of said proportion falls below a given level L, and $L_A$ and $L_B$ being the values of L which respectively correspond to $N_A$ and $N_B$.

2. A method according to claim 1, in which the same beam of light is used in the derivation of both said test signal and the signal which is analysed.

3. A method according to claim 2, in which the signal which is analysed and said test signal are respectively derived by means of two consecutive scans of said surface which respectively involve movements of said spot in opposite senses along the same path on said surface.

4. A method according to claim 1, in which said surface is the surface of a cylinder bore, and said spot is caused to scan over said surface along a helical path having a pitch less than the diameter of said spot.

5. An apparatus for use in the inspection of machined surfaces, the apparatus comprising:

scanning means for generating electrical signals in respect of a surface to be inspected by causing an illuminated spot formed by a beam of light to scan over said surface and detecting the resultant variations of the proportion of the incident light returned from said spot;

means for analysing a first signal generated by said scanning means in respect of a given surface to obtain data from which may be deduced the value of the expression $$\frac{L_B \ln(N_A) - L_A \ln(N_B)}{\ln(N_A/N_B)},$$

$N_A$ and $N_B$ being different values of N, where N is the fraction of the total length of the scan for which the value of said proportion falls below a given level L, and $L_A$ and $L_B$ being the values of L which respectively correspond to $N_A$ and $N_B$;

means for sensing excursions in a second signal generated by said scanning means in respect of said given surface, said excursions corresponding to decreases of said proportion below a threshold level; and means for setting said threshold level substantially to the value of said expression indicated by said data.

* * * * *